US009463493B1

United States Patent
Arlinghaus et al.

(10) Patent No.: US 9,463,493 B1
(45) Date of Patent: Oct. 11, 2016

(54) METHOD OF PRODUCING GLUTEN FREE OATS

(71) Applicant: General Mills Inc., Minneapolis, MN (US)

(72) Inventors: Mark A Arlinghaus, Minneapolis, MN (US); Troy D Bierbaum, Brooklyn Park, MN (US); Christine M Nowakowski, Plymouth, MN (US); Daniel J Winderl, Plymouth, MN (US); Philip K Zietlow, Wayzata, MN (US)

(73) Assignee: General Mills, Inc., Minneapolis, MN (US)

( * ) Notice: Subject to any disclaimer, the term of this patent is extended or adjusted under 35 U.S.C. 154(b) by 380 days.

(21) Appl. No.: 13/782,497

(22) Filed: Mar. 1, 2013

Related U.S. Application Data

(60) Provisional application No. 61/605,561, filed on Mar. 1, 2012.

(51) Int. Cl.
*B07C 5/00* (2006.01)
*B07C 5/342* (2006.01)

(52) U.S. Cl.
CPC .................................. *B07C 5/3425* (2013.01)

(58) Field of Classification Search
CPC ..................... B07C 5/3425; G01N 2021/1706; G01N 2021/8592; G01J 3/42
USPC ........ 209/576, 577, 586, 587, 659; 356/320, 356/432
See application file for complete search history.

(56) References Cited

U.S. PATENT DOCUMENTS

| 4,260,262 | A |   | 4/1981 | Webster |
|---|---|---|---|---|
| 5,638,961 | A |   | 6/1997 | Satake et al. |
| 5,761,070 | A |   | 6/1998 | Conners et al. |
| 5,779,058 | A | * | 7/1998 | Satake et al. ................. 209/581 |
| 5,991,025 | A |   | 11/1999 | Wright et al. |
| 6,013,887 | A | * | 1/2000 | Satake et al. ................. 209/581 |

(Continued)

OTHER PUBLICATIONS

Mohan et al., "*Classification of Bulk Cereals Using Visible and NIR Reflectance Characteristics*", Canadian Biosystems Engineering, vol. 47, pp. 7.7-7.14, 2005.

*Primary Examiner* — Joseph C Rodriguez
*Assistant Examiner* — Kalyanavenkateshware Kumar
(74) *Attorney, Agent, or Firm* — Diederiks & Whitelaw, PLC; Gregory P. Kaihoi, Esq.

(57) ABSTRACT

The separation of oats from a combination of grains is performed by obtaining optical data includes both reflectance data and visual data and then analyzing the data in multiple ways, including analyzing information obtained based on ratios of wavelengths and grain imagery. The reflectance data relies on near infrared spectroscopy at requisite ratios of wavelengths in the range of 1100 nm to 2200 nm, while the grain imagery encompasses images of both sides of each of the combination of grains and can also take into account grain size and shape differentiations. The results is an oats separation process wherein at least 99% of foreign grains are rejected with only about 3% of the oats being rejected, while enabling volume processing of grains and establishing a supply of oats with a gluten level well below 20 ppm.

8 Claims, 1 Drawing Sheet

(56) References Cited

U.S. PATENT DOCUMENTS

| | | |
|---|---|---|
| 6,100,526 A | 8/2000 | Mayes |
| 7,016,043 B2 * | 3/2006 | Fukumori et al. ............ 356/432 |
| 7,202,434 B2 | 4/2007 | Löfqvist et al. |
| 7,417,203 B2 * | 8/2008 | Lofquist et al. .............. 209/576 |
| 7,858,893 B1 | 12/2010 | Haff et al. |
| 8,045,168 B2 | 10/2011 | Missotten et al. |
| 2004/0055211 A1 | 3/2004 | Lestander et al. |
| 2006/0064780 A1 | 3/2006 | Munck et al. |

\* cited by examiner

METHOD OF PRODUCING GLUTEN FREE OATS

CROSS-REFERENCE TO RELATED APPLICATION

The present application claims the benefit of U.S. Provisional Patent Application Ser. No. 61/605,561 which was filed Mar. 1, 2012 and entitled "Method of Producing Gluten Free Oats."

BACKGROUND OF THE INVENTION

In general, the invention is concerned with grain sorting techniques and, more particularly, with methods to sort grains in order to produce gluten free oats.

Sensitivity to gluten is estimated at afflicting up to 2% of the population. In fact, based on the increased awareness of Celiac disease and gluten intolerance, gluten levels in certain foods can be a limiting factor in consumption. Oats themselves do not contain gluten. However, oats cultivated in North America, Europe and even other parts of the world are commonly contaminated by gluten containing foreign grains, including wheat, barley, rye and triticale. These foreign grains typically exhibit about 14% by weight protein, with 40% of the protein being attributable to gluten such that approximately 5.6% by weight of the grains is gluten. This contamination is commonly known to come from various sources, mainly from the rotation of small grain crops on the same land, with residual contaminating seeds germinating with a seeded oat crop. In addition, contamination from other grains which are harvested, transported, stored and merchandized in common with oats is a contributing factor. As a result, it is not uncommon to find from 0.5% to 5.0% of these other grains mixed with commercially marketed oats. Therefore, absent dedicating land, harvesting equipment, transporting vehicles, storage units, packaging and production facilities, and the like only for use in connection with oats, cross contamination is inevitable.

Although the federal government has not finalized rules for labeling products "gluten-free", the American regulations will likely be similar to the Codex rules established in Europe, which stipulate a maximum of 20 ppm gluten in "gluten-free" food products. Based on draft proposals from the United States Food and Drug Administration, oats will continue to be eligible for gluten-free labeling as long as they are substantially free of foreign seeds. With this in mind, separating oats from foreign grains and other contaminants is required if oat products are to be produced to mandated gluten levels.

Known grain sorting techniques typically rely on mechanical or optical systems. Mechanical systems are considered advantageous generally based on their simplicity and cost benefits. However, simply put, previous attempts to employ mechanical sorting machines have failed to consistently deliver a high yield of oats without undesirably high levels of gluten contaminants. Optical systems generally employ multiple cameras to view grain falling toward a grain rejection mechanism. In some machines, duplicate optical units are positioned on opposite sides of a sorter to provide simultaneous images of opposing sides of the grains. In general, optical sorters have higher associated costs and known optical sorters also have not been sufficiently effective in achieving the reduced gluten levels desired in accordance with the invention. Therefore, there is seen to exist a need to provide a method for effectively and efficiently decontaminating oat grains in order to produce a high yield of gluten-free oats useable for various purposes, particularly as an oat ingredient in the production of various food products, including cereal and granola.

SUMMARY OF THE INVENTION

The invention is directed to removing foreign grains from oats to ensure gluten levels below 20 ppm, and preferably no greater than 10 ppm. In efforts to dramatically improve foreign material removal from the oats, near infrared spectroscopy is employed for identifying the common contaminants (particularly wheat, barley, rye, and triticale). More specifically, the invention partially concerns the preparation of gluten free oats using optical sorters, such as Sortex optical sorters, equipped with near infrared cameras operating in the range of 1100 nm to 2200 nm. Discriminant or other forms of analysis are performed on the obtained data.

In accordance with another aspect of the invention, the grain sorting method uses near infrared reflectance data at just two wavelengths to accurately distinguish oats from contaminant grains. For instance, commercially available InGaAs line scan cameras with band pass filters centered at 1220 nm and 1460 nm are considered to work well for full scale machines. Specifically, the dual wavelength near infrared reflectance data is obtained from measurement from both sides of each seed. In a variant of the invention, sorting purity and yield is enhanced by adding size and shape data to a sorting algorithm, with the size and shape data being extracted from the infrared camera data or by the use of additional visible spectrum cameras. In further accordance with the invention, the multi-side data can be obtained employing ratios of different wavelengths to even further enhance the sorting purity and yield. Overall, the invention enables bulk volume processing of grains to establish gluten-free oats. In fact, discriminant analysis on current laboratory data set yields better than 99% rejection of foreign seeds while retaining 97% of the good oats.

Additional objects, features and advantages of the present invention will become more readily apparent from the following detailed description of the invention with reference to the drawings.

DETAILED DESCRIPTION OF THE INVENTION

Figure 1:
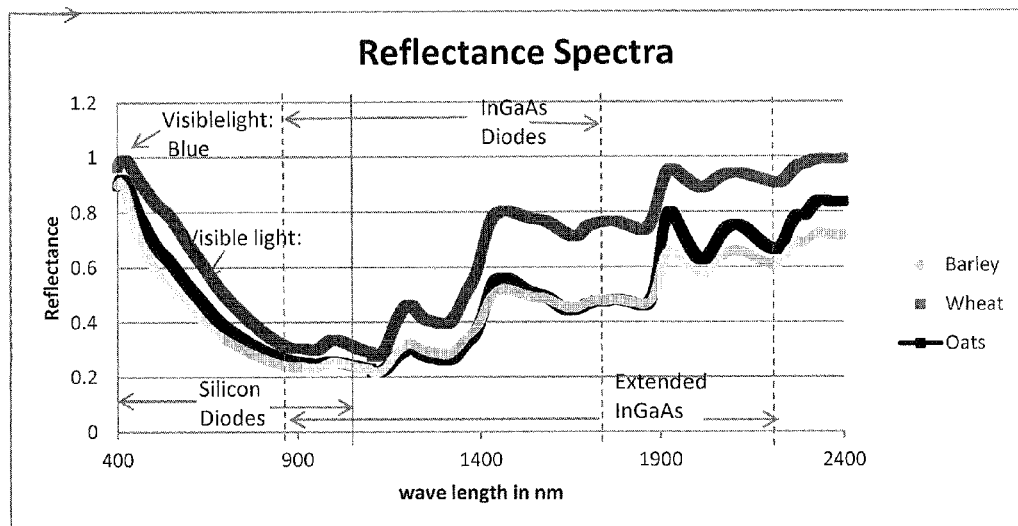
FIG. 1 is a graph of reflectance spectra for various common grains, particularly oats, barley and wheat.

In connection with removing foreign grains from oats to ensure gluten levels below 20 ppm, and preferably below 10 ppm, the invention employs optical sorters, such as Sortex optical sorters, equipped with near infrared cameras operating in the range of 1100 nm to 2200 nm. Overall, it is desired to employ grain sorting methods which limit the number of necessary modifications to traditional grain sorters thereby minimizing associated costs, while accurately distinguishing oats from contaminant grains using near infrared reflectance data at just two wavelengths, with both sides of a seed being measured. By not requiring full spectral data sets, the cost and speed restrictions of true hyperspectral imaging systems can be avoided. In one form of the invention, commercially available InGaAs line scan cameras with band pass filters centered at 1220 nm and 1460 nm are employed in connection with full scale machines. Sorting purity and yield is improved by adding size and shape data to the sorting algorithm. The size and shape data can be extracted from the infrared camera data or by the use of additional visible spectrum cameras. In accordance with another aspect of the invention, visible spectrum cameras are also used to obtain image data of both sides of the grains. The reflectance and image data are effectively processed to yield better than 99% rejection of foreign seeds while rejecting only about 3% of the good oats. More particularly, both near infrared spectroscopy at requisite ratios of wavelengths and visual imagery are employed in connection with algorithms for identifying and separating the common contaminants (particularly wheat, barley, rye and triticale). Overall, the invention enables bulk volume processing of grains to establish gluten-free oats, with volume processing meaning the analysis of a minimum of 165000 grains/minute per camera and generally up to 1633500 grains/minute per camera.

In general, the components of the optical systems employed, as well as the analytical software, are known and therefore not considered part of the invention. Instead, it is the type and manner of processing of the data to which the present invention is particularly directed. Specifically, as indicated above, the dual wavelength, near infrared reflectance data is obtained from measurement from both sides of each seed, with the signals from both sides being analyzed together. More specifically, the multi-side data is obtained employing ratios of different wavelengths to even further enhance the sorting purity and yield. By adding the size and shape data, as well as visual image data taken from both sides of each seed or grain for use in a sorting algorithm, the method of the invention effectively provides for establishing a supply of gluten free oats. Therefore, in accordance with the invention, statistical analysis, such as discriminant analysis, is applied to both reflectance and visual data collected from individual seed kernels to yield extremely high foreign grain identification accuracies in volume processing of contaminated oats. In fact, as will be detailed below, analysis on current reflectance laboratory data yielded better than 99% rejection of foreign seeds while retaining 97% of the good oats and providing cleansed oats to actually better than 10 ppm gluten.

Reference will now to made to exemplary sorting operations performed in accordance with the invention.

A. Sorting Example I

In connection with this exemplary experiment, it should initially be noted that the starting seed/grain sample set was composed of oats (880 samples), barley (641 samples of 2 row, 6 row, and non specified barley), and wheat (230 samples composed of spring and winter, red and white, hard and soft). Oat samples were taken across crop years and at multiple elevators. Barley samples were mostly purpose grown 2 row and 6 row cultivars, but also included 130 seeds collected as contaminants from oat samples. A few rye samples were included. At this point, it is mentioned that rye and triticale were found to be easily differentiated from oats such that more focus was actually placed on the barley and wheat.

This example began by measuring single seed NIR spectra from 1100 to 2500 nm on an optical sorter, specifically a Buchi 500, in reflectance mode. A total of 1760 seeds were measured. Spectral peaks were identified using first derivatives of the scans, and principle components analysis was used on the peaks to determine which subsets of the data would yield the best results. After the best candidates were identified, linear discriminant analysis was performed on both the raw data and on ratios of the candidate peaks. The ratios of peak heights were reviewed on the grounds that these would be less sensitive to variations in lighting conditions than the absolute values of the peaks. FIG. 1 shows the reflectance spectra for various common grains, particularly oats, barley and wheat, in this case for bulk samples. FIG. 1 also indicates which of the economical photo-sensor materials cover the various wavelengths.

Spectral peaks for oats were found at 1104, 1211, 1308, 1460, 1653, 1736, 1849, 1929, 2016, 2097, 2216, 2385 and 2500 nm. Although all these peaks could be considered helpful in differentiating seeds, the invention particularly concentrates on employing ratios of wavelengths, such as wavelength ratios centered around 1211, 1460 and/or 1653 nm. That is, employing ratios of wavelengths has been determined to be highly effective, while exhibiting an advantage of working in a standard InGaAs range. When using extended InGaAs cameras, the ratios of 1929, 2016, and 2097 also yielded good results. Table 1 shows an output file from linear discriminate analysis on the full data set. The inputs were the ratios of the peak heights 1460 nm/1211 nm, 1653 nm/1211 nm, 1653 nm/1460 nm, 1211 nm/1460 nm and 1211 nm/1653 nm. Of the 844 non-oat seeds, only 2 (0.24%) were incorrectly identified as oats. True oats were rejected as foreign grains 3.7% of the time. Similar results are obtained when using the set of higher wavelengths. As set forth above, considerable focus was given to choosing peaks that can tell barley from oats. Basically, although wheat can be commonly found in supplies of oats, the geometric distance of the spectral vectors between wheat and oats is much greater than the distance between oats and barley. This is true of the raw vectors and the linearly transformed vectors used in PCA and discriminant analysis. Rye and triticale are similarly easy to tell from oats. Thus, efforts were made to tweak the algorithm for better performance against barley knowing that a decrease in power against wheat will still yield accurate rejections. In addition, in connection with the base invention, it should be recognized that misclassification among the gluten containing seeds was not a concern. Therefore, a wheat kernel identified as a barley kernel which is still rejected is a positive result.

TABLE 1

Discriminant analysis using ratios of peaks at 1211, 1460 and 1653 nm.

| Put into Group | True Group | | | | | |
| --- | --- | --- | --- | --- | --- | --- |
|  | 2RB | 6RB | b | o | r | w |
| 2RB | 178 | 77 | 35 | 0 | 1 | 0 |
| 6RB | 24 | 63 | 22 | 0 | 0 | 0 |
| b | 33 | 95 | 65 | 35 | 1 | 2 |
| o | 0 | 1 | 1 | 842 | 0 | 0 |
| r | 13 | 24 | 7 | 0 | 5 | 62 |
| w | 2 | 1 | 0 | 3 | 3 | 166 |
| Total N | 250 | 261 | 130 | 880 | 10 | 230 |

TABLE 1-continued

Discriminant analysis using ratios of peaks at 1211, 1460 and 1653 nm.

| | True Group | | | | | |
|---|---|---|---|---|---|---|
| Put into Group | 2RB | 6RB | b | o | r | w |
| N correct | 178 | 63 | 65 | 842 | 5 | 166 |
| Proportion | 0.712 | 0.241 | 0.500 | 0.957 | 0.500 | 0.722 |

2RB = 2 row, 6RB = 6 row, b = barley of unknown type, o = oats, r = rye, w = wheat of all kinds.

Although results leading to efficient and accurate machines would be considered successful, it is desired in accordance with an aspect of the invention to actually establish a method providing for high speed seed sorting. Therefore, to further this object of the invention, a principle of optically monitoring a monolayer of grains cascading off a chute (e.g., Sortex Z series) is employed. However, instead of color cameras or monochromatic InGaAs cameras, one form of the invention employs a system of band-pass filtered line scan cameras mounted such that they focus on the same spot. Although this design has the advantage that it can rely on well established hardware, but it is not without challenges. In particular, it has been found that reliance on this aspect of the invention would experience higher rejection rates than certain known grain sorting arrangements. Based on the actual foreign grain content in the incoming oats being 1 to 2% and the incorrect identification of 3 to 5% of oats as barley, the employed ejectors must attempt to remove 4 to 7% of the incoming stream. In order to ensure that grains are rejected, air blasts typically cover an area ahead and behind the kernel. When the widened air pulses knock out nearby grains, this results in a risk of a total rejection level well above 7%. Therefore, this aspect assures the high level of foreign grain removal at the potential expense of the removal of certain oats as well. However, through recycling, the rejected grains can be re-scanned to reduce losses at the expense of total system throughput.

With the above in mind, it should be understood that the identification using linear discriminate analysis on combinations of the spectral bands and ratios of various spectral bands in accordance with the invention can be employed to achieve false positive identification of oats of less than 1 per 100 contaminant seeds and false negative oat identifications of less than 6% of the oats. For instance, statistical techniques using spectra collected on hyper-spectral cameras instead of FT-NIR units could be performed. In addition, the invention can be employed with expanded frequency bands, including on band-pass filtered line scan cameras, with the performance of the line scan cameras being based on scan rates and lighting conditions. Although the invention has been described with reference to 1200, 1460 and 1650 nm as spectral bands that work well within a standard InGaAs sensor range and 1930, 2020 and 2100 nm in extended range InGaAs sensors, spectral bands 40 nm wide centered on the 1200, 1300, 1460, 1850, 1930, 2020, 2220 and 2390 nm could be employed, particularly through the ratio of wavelength aspect of the invention as detailed above.

B. Sorting Example II

In the above oat sorting example, the reflectance spectrum of grains and the ability to use linear discriminant analysis is employed to distinguish oats form other grains. Although it is set forth that the spectral information at wavelengths over 1680 nm can be used to sort seeds, the cameras needed to collect data at those wavelengths are significantly more expensive than standard InGaAs cameras operating from 1000 to 1680 nm. Therefore, there is certainly advantages to focus on the spectral features centered on 1020 nm, 1130 nm, 1220 nm, 1320 nm, 1475 nm and 1680 nm.

In connection with this example, a sample set of 500 barley seeds and 500 oats was prepared by measuring the top and bottom of each seed on a Buchi 500. The bottom of the seed was established as the crease side of the barley and the side of the oat where the outermost layer of hull is split. The wavelengths listed above were found by taking first derivatives of the spectra and looking for zero values. Reflectance values for the spectral features were calculated by using a boxcar filter centered on the above wavelengths and extending +/−20 nm from each wavelength, with combinations of the features two at a time. Single sided measurements on the tops of the seeds at 1200 and 1475 nm produced outstanding results. Bottom side measurements at those frequencies were not as good. Since side presentation to the camera cannot be effectively controlled, the invention captures both sides with opposing cameras. In accordance with the preferred form, an average value from the opposing side cameras are used to determine the seeds to be rejected. The results are shown in Table 2.

TABLE 2

Discriminant analysis using reflectance data at 1220 and 1475 nm. For each seed, measurements from the front and back were averaged.

| | True Group | |
|---|---|---|
| Put into Group | Bar | Oats |
| Bar | 498 | 10 |
| O | 2 | 350 |
| Total N | 500 | 360 |
| N correct | 498 | 350 |
| Proportion | 0.996 | 0.972 |

N = 860
N Correct = 848
Proportion Correct = 0.986

At this point, it should be recognized that various types of scan cameras can be employed, including hyper-spectral cameras, filtered area scan, and filtered monochromatic line scan cameras. In fact, certain experiments were actually conducted using a Specim hyper-spectral camera with a push broom stage to capture full spectral data at a physical resolution of 10 pixels per mm and a spectral resolution of 320 readings over 1000 to 2400 nm. In certain embodiments, readings were taken on only one side of the seed, and the reflectance values at each pixel were averaged to yield a single reflectance value for the entire seed. This information was then used in combination with size and shape data. For the size and shape data, the seeds were actually scanned on a flat bed scanner to get size and shape data as the seeds were not considered to be positioned in an orientation which would present their narrowest view to the hyper-spectral camera. That is, because barley seeds are wider than oats, it is desired to ensure a comparison of the narrowest view of the barley to the oats to ensure that the predictions made were on the conservative side. Table 3 shows that even single sided measurements produce good results when combined with shape data. The barley rejection percent rises to 99% when a "box x/y" ratio is used instead of an aspect ratio in the Image Pro Plus software. Of course, since the barley would likely be presented with their crease pointing directly toward or away from one camera, the full scale separation effectiveness based on shape will be more effective. With this knowledge and the fact that oats fill rectangles better than barley, these facts are useful in sorting.

TABLE 3

Discriminant Analysis with 1220 nm, 1475 nm, Aspect ratio and Area/Box as inputs

| Put into Group | True Group | |
|---|---|---|
| | b | o |
| b | 83 | 3 |
| o | 2 | 47 |
| Total N | 85 | 50 |
| N correct | 83 | 47 |
| Proportion | 0.976 | 0.940 |

N = 135
N Correct = 130
Proportion Correct = 0.96

Figure 2:
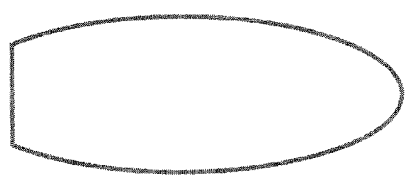
FIG. 2 illustrates an image of an oat grain.
Figure 3:
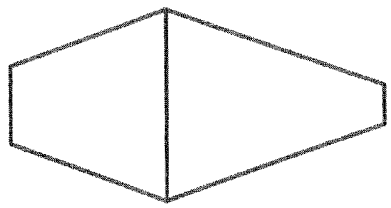
FIG. 3 illustrates an image of a barley grain.

If computational time is not a limit, more sophisticated shape recognition algorithms can be used. Oats tend to look like ellipses with a flattened end while barley can be generalized as a combination of two trapezoids. See FIGS. 2 and 3. The barley shape is defined by five parameters: length of each trapezoid, width of each trapezoid at the ends, and the common width of the trapezoid bases. With this in mind, the best fit of these parameters to the measured seed is found in accordance with the invention. Once this is done, the difference between the actual seed outline and the estimated outline can be calculated. Basically, barley has a smaller difference than oats. Typical image analysis preprocessing, such as erosion and dilation, can also be employed to remove artifacts from stray chaff and hulls.

Based on the above, it should be readily apparent that size and shape data is clearly helpful for sorting. Certainly, the resolutions employed could vary. For instance, various scans were captured at 300 pixels per inch, with 50 pixels per inch as a more economical target. In any case, overall, the invention sets forth a method of separating oats from gluten containing seeds by using near infrared reflectance data and image data, preferably on both sides of the seeds. The invention includes both types of data collected to differentiate the seeds and the statistical methods used to interpret that data. The data collected includes near infrared reflectance intensities over specific bands of wavelength. Broadly, the oat and barley spectra contains maxima or minima inflection points of interest at 1020, 1130, 1220, 1320, 1475, 1680, 1880, 1930, 2020, 2110 and 2230 nm, but it is ratios of these wavelengths which establish the data being fully analyzed, with reflectance intensity being the inputs for discriminant analysis that serves as the decision criterion for accepting or rejecting seeds. Capturing multiple views of the same seed, specifically from distinct angles and most preferably from both sides of the seed, such as two pairs of cameras viewing opposite sides of the seed at 1220 and 1475 nm wavelengths and averaging the spectral data from the two sides, and adding these measurements to the analysis further improves the quality of the separation. The practicalities of lighting and optical filter design require that the cameras respond not just to a single wavelength of light, but to a range of wavelengths. The preferred range is +/−20 nm from the feature's wavelength, although good separations can still be achieved with wider bands. Separation quality can be improved by adding shape data to the discriminant analysis, with useful shape data mainly including seed size information such as length, width and aspect ratio. These may be calculated using a variety of techniques, but preferably through fitting ellipses and taking the major and minor axes or fitting rectangles and taking the length of the sides. Overall, these sorting techniques define individually respectable results but have been found to combine synergistically to produce better than 99% rejection of foreign seeds while retaining 97% of the good oats at volume processing levels to provide cleansed oats at less than 10 ppm gluten.

Although described with reference to preferred embodiments and aspects of the invention, it should be understood that various changes and/or modifications to the invention can be made without departing from the spirit of the invention. For instance, binary decision trees can be employed as an alternative to linear discriminant analysis (LDA), particularly since data scatter in the oats is not identical to the barley. In addition, quadratic discriminant analysis or optimal discriminant analysis could also be employed. In general, the invention is only intended to be limited by the scope of the following claims.

We claim:

1. A method of producing gluten-free oats from a combination of grains comprising:
   obtaining optical data on the combination of grains, wherein the optical data includes both reflectance data and visual data;
   analyzing the reflectance data utilizing information based on ratios of wavelengths;
   analyzing the visual data through images of both sides of each of the combination of grains; and
   separating the oats from the combination of grains to establish a supply of oats having a gluten level below 20 ppm based on the analysis of both the reflectance and visual data.

2. The method of claim 1, wherein the optical data is obtained utilizing near infrared cameras operating in the range of 1100 nm to 2200 nm.

3. The method of claim 1, wherein the ratios of wavelengths are selected from the group consisting of 1460 nm/1211 nm, 1653 nm/1211 nm, 1653 nm/1460 nm, 1211 nm/1460 nm, and 1211 nm/1653 nm.

4. The method of claim 1, further comprising: extracting size and shape information from the optical data, wherein separating the oats is further performed based on the size and shape information.

5. The method of claim 1, wherein separating the oats from the combination of grains constitutes rejecting at least 99% of foreign grains while rejecting only about 3% of the oats.

6. The method of claim 1, wherein separating the oats from the combination of grains results in oats with a gluten level of no greater than 10 ppm.

7. The method of claim 1, further comprising: employing discriminant analysis in analyzing the optical data.

8. The method of claim 1, wherein the oats are separated from the combination of grains through volume processing.

* * * * *